United States Patent [19]

Klemann et al.

[11] Patent Number: 5,068,119
[45] Date of Patent: Nov. 26, 1991

[54] ACID-HYDROLYZABLE ESTER DERIVATIVES AS LOW CALORIE FAT MIMETICS

[75] Inventors: Lawrence P. Klemann, Somerville; John W. Finley, Whippany, both of N.J.

[73] Assignee: Nabisco Brands, Inc., Parsippany, N.J.

[21] Appl. No.: 590,298

[22] Filed: Sep. 28, 1990

[51] Int. Cl.$^5$ .............................................. A23D 9/00
[52] U.S. Cl. .................................. 426/601; 426/611; 426/804
[58] Field of Search ............... 426/611, 612, 804, 601, 426/566; 260/410.7, 410.8

[56] References Cited

U.S. PATENT DOCUMENTS

| | | |
|---|---|---|
| 519,980 | 5/1894 | Winter . |
| 2,962,419 | 11/1960 | Minich .................................. 167/81 |
| 3,495,010 | 2/1970 | Fossel ................................... 424/312 |
| 3,579,548 | 5/1971 | Whyte .............................. 260/410.7 |
| 3,600,186 | 8/1971 | Mattson et al. ............................ 99/1 |
| 3,637,774 | 1/1972 | Babayan et al. ................. 260/410.6 |
| 3,876,794 | 4/1975 | Rennhard .............................. 426/152 |
| 4,005,195 | 1/1977 | Jandacek ............................. 424/180 |
| 4,304,768 | 12/1981 | Staub et al. ......................... 424/180 |
| 4,355,032 | 10/1982 | Verheyden .......................... 424/253 |
| 4,482,927 | 11/1984 | Melby et al. .......................... 360/40 |
| 4,508,746 | 4/1985 | Hamm ................................. 426/601 |
| 4,582,927 | 4/1986 | Fulcher ............................... 560/201 |
| 4,797,300 | 1/1987 | Jandacek et al. ................... 426/529 |
| 4,830,787 | 5/1989 | Klemann et al. ................... 260/410 |
| 4,840,815 | 6/1989 | Meyer et al. ........................ 426/611 |
| 4,849,242 | 7/1989 | Kershner ............................. 426/601 |
| 4,861,613 | 8/1989 | White et al. ........................ 426/611 |
| 4,915,974 | 4/1990 | D'Amelia et al. ................. 426/611 |
| 4,927,659 | 5/1990 | Klemann et al. ................... 426/611 |

FOREIGN PATENT DOCUMENTS

| | | |
|---|---|---|
| 1106681 | 8/1981 | Canada . |
| 0072027 | 2/1982 | European Pat. Off. . |
| 0074306 | 3/1982 | European Pat. Off. . |
| 0049072 | 4/1982 | European Pat. Off. . |
| 187297 | 7/1986 | European Pat. Off. . |
| 205273 | 12/1986 | European Pat. Off. . |
| 233856 | 8/1987 | European Pat. Off. . |
| 3529564 | 3/1987 | Fed. Rep. of Germany . |

OTHER PUBLICATIONS

Aserin, A., et al., Ind. Eng. Chem. Prod. Res. Dev. 23: 452-454 (1984).
Booth, A. N., and Gros, A. T., 40 J. Amer. Oil Chem. Soc. 551-553 (1963).
Goodman and Gilman's Pharm. Basis of Therapeutics, 7th ed. Macmillian Publishing Co., New York 1002-1003 (1985).
Gottenbos, J. J., Chap. 8 in Beare-Rogers, J., ed., Dietary Fat Requirements in Health and Development, A.O.C.S. 107-112 (1988).
Hamm, D. J., 49 J. Food Sci. 419-428 (1984).
Haumann, B. J., 63 J. Amer. Oil Chem. Soc., pp. 278-287 (1986).
Hashim, S. A. and Babayan, V. K., 31 Amer. J. Clin. Nutril S273-276 (1978).
La Barge, R. G., 42 Food Tech. 84-90 (1988).
Mead, J. et al., Lipids, Plenum, New York, pp. 459-473 (1986).
Stryker, W. A., 31 Arch. Path 670-692 (1941).
Dorland's Medical Dictionary, 27th ed., W. B. Saunders Co., Philadelphia, p. 759 (1988).

Primary Examiner—Donald E. Czaja
Assistant Examiner—John Mowbray

[57] ABSTRACT

Acid-hydrolyzable ester derivatives, notably compounds having the following formula

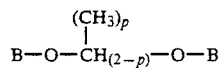

where

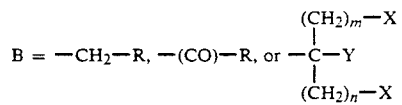

X = H, an alkyl having 1 to 4 carbons, —O—(CO)—R, or —(CO)—O—R, or mixtures thereof,
Y = H, an alkyl having 1 to 4 carbons, or —(CO)—O—R,
R = an aliphatic group having 1 to 29 carbons,
m = 0, 1, or 2,
n = 0, 1, or 2, and
p = 0, 1, or 2, are a new class of edible fat mimetics suitable for use in neutral or alkaline food compositions.

22 Claims, No Drawings

ACID-HYDROLYZABLE ESTER DERIVATIVES AS LOW CALORIE FAT MIMETICS

BACKGROUND OF THE INVENTION

This invention relates to the use of acid-hydrolyzable esters comprising compounds having two alkyl groups bearing pendant ester groups, aliphatic groups, or acyl groups, or mixtures thereof, linked together by means of an acid labile linkage of the formula, $$-O-(C(CH_3)_pH_{2-p})-O-$$

where p=0 to 2, as edible, preferably partially digestible, fat mimetics suitable for use in neutral or alkaline food compositions.

Dietary fat is the most concentrated source of energy of all the nutrients, supplying 9 kcal/gram, about double that contributed by either carbohydrate or protein. The amount of fat in the American diet has increased in the last 60 years by about 25% (Mead, J., et al. Lipids, Plenum, N.Y., 1986, page 459), so that fats now provide approximately 40% (or more) of the daily caloric intake. Moreover, technological advances in the food industry, including efficient and safe hydrogenation procedures, have changed the kind of fat in foods.

Because fats are high in calories and because certain fats appear to pose a health risk when consumed in large quantities over time, a number of national advisory committees on nutrition have made recommendations differing in detail, but the common theme is a reduction in the total amount of fat in the diet (Gottenbos, J. J., chapter 8 in Beare-Rogers, J., ed., *Dietary Fat Requirements in Health and Development*, A.O.C.S. 1988, page 109). Yet fat contributes to the palatability and flavor of food, since most food flavors are fat-soluble, and to the satiety value, since fatty foods remain in the stomach for longer periods of time than do foods containing protein and carbohydrate. Furthermore, fat is a carrier of the fat-soluble vitamins, A, D, E, and K, and the essential fatty acids, which have been shown to be important in growth and in the maintenance of many body functions. Hence, major research efforts have focused on ways to produce food substances that provide the same functional and organoleptic properties as fats, but not the calories.

A number of fat replacements have heretofore been suggested (recently reviewed by Hamm, D. J., 49 *J. Food Sci.* 419 (1984), Haumann, B. J., 63 *J. Amer. Oil Chem. Soc.* 278 (1986) and LaBarge, R. G., 42 *Food Tech.* 84 (1988)). Hamm divides replacement fats into two broad categories: structurally reengineered triglycerides modified to retain their conventional functional properties in foods, while removing their susceptibility toward hydrolysis or subsequent absorption during digestion, and materials developed from chemistry unrelated to triglycerides.

Examples of the former class of triglyceride analogues include compounds having the glycerol moiety replaced with alternate polyols (e.g., pentaerythritol in U.S. Pat. No. 2,962,419 to Minich, or sugars in U.S. Pat. No. 3,600,186 to Mattson and Volpenhein and U.S. Pat. No. 4,840,815 to Meyer, et al.); compounds having the fatty acids replaced with alternate acids (e.g., branched esters as described in U.S. Pat. No. 3,579,548 to Whyte); compounds having insertions between the glycerol and the fatty acid (e.g., ethoxy or propoxy groups in U.S. Pat. No. 4,861,613 to White and Pollard); compounds having reversed esters (e.g., malonates in U.S. Pat. No. 4,482,927 to Fulcher, trialkoxytricarballylates in U.S. Pat. No. 4,508,746 to Hamm and carboxy/carboxylates in U.S. Pat. No. 4,830,787 to Klemann and Finley); and compounds having the ester bonds replaced by ether bonds (Can. Pat. No. 1,106,681 to Trost).

Examples of the latter category of fat replacements chemically unrelated to triglycerides are mineral oil (suggested as early as 1894 in U.S. Pat. No. 519,980 to Winter); polyglucose and polymaltose (U.S. Pat. No. 3,876,794 to Rennhard); jojoba wax (W. Ger. Pat. No. 3,529,564 to Anika); polyoxyalkylene esters (U.S. Pat. No. 4,849,242 to Kershner); polyvinyl alcohol esters (U.S. Pat. No. 4,915,974 to D,Amelia and Jacklin), and polysiloxane (Eur. Pat. Ap. No. 205,273 to Frye).

Nondigestible or nonabsorbable edible fat replacements have proved disappointing when tested in feeding trials, where gastrointestinal side effects occurred, in some cases so extreme that frank anal leakage was observed. Nondigestible fats appear to act as a laxative and are expelled from the body, eliciting foreign body reactions like those early documented for mineral oil (Stryker, W. A., 31 *Arch. Path.* 670 (1941), more recently summarized in Goodman and Gilman's *Pharmacological Basis of Therapeutics*, 7th ed., Macmillan Pub. Co., N.Y. 1985, pp. 1002-1003). In the U.S.D.A.,s assessment of the caloric availability and digestibility of a series of new-type fats in the 1960's (e.g., amylose fatty acid esters, diglyceride esters of succinic, fumaric, and adipic acids, and polymeric fats from stearic, oleic and short-chain dibasic acids; see Booth, A. N., and Gros, A. T., 40 *J. Amer. Oil Chem. Soc.* 551 (1963) and the references cited therein), rats fed the experimental fats exhibited undesirable gastrointestinal side effects similar to what had already been observed with mineral oil consumption by people. In several of the balance studies, the diarrhea was so extreme that digestibility coefficients could not be calculated in the trial feedings (ibid., Table I, p. 552).

Polyglycerol and polyglycerol esters, suggested as fat replacements by Babayan and Lehman (U.S. Pat. No. 3,637,774), have been suggested for use as fecal softening agents as well (U.S. Pat. No. 3,495,010 to Fossel). A number of remedies have been recommended to combat the anal leakage observed when sucrose polyesters are ingested (e.g., employing cocoa but ters, U.S. Pat. No. 4,005,195 to Jandacek, incorporating saturated fatty groups, Eur. Pat. Ap. No. 233,856 to Bernhardt, or mixing residues, U.S. Pat. No. 4,797,300 to Jandacek, et al.), and dietary fiber preparations have been incorporated into polysaccharide and/or polyol-containing foodstuffs to help inhibit the diarrheal effect (U.S. Pat. No. 4,304,768 to Staub et al.). Partially digestible fat replacements have also been suggested (U.S. Pat. No. 4,830,787 to Klemann and Finley; U.S. Pat. No. 4,849,242, cited above; and U.S. Pat. No. 4,927,659 to Klemann, et al.).

SUMMARY OF THE INVENTION

An object of the present invention is to provide a unique approach to the structuring of edible fat mimetics by suggesting compounds having two alkyl groups bearing pendant ester groups, aliphatic groups, or acyl groups, or mixtures thereof, linked together by means of an acid labile linkage of the formula

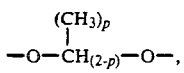

It is another object of the present invention to provide a new group of partially digestible edible fat replacement compounds which can have functional groups tailored to modulate caloric availability, while minimizing laxative side effects.

These and other objects are accomplished by the present invention, which describes acid-hydrolyzable ester derivatives, a new class of edible synthetic fat mimetics, methods of using them, and food compositions incorporating them. These compounds have an acid-hydrolyzable linkage,

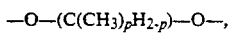

where $p = 0$ to 2,
attaching two alkyl groups bearing pendant ester groups, aliphatic groups or acyl groups, or mixtures thereof. The new fat mimetic compounds have the general formula

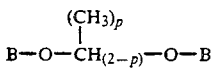

where

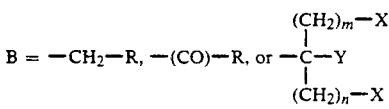

$X = H$, an alkyl having 1 to 4 carbons, —O—(CO)—R, or —(CO)—O—R, or mixtures thereof,
$Y = H$, an alkyl having 1 to 4 carbons, or —(CO)—O—R,
$R =$ an aliphatic group having 1 to 29 carbons,
$m = 0$, 1, or 2,
$n = 0$, 1, or 2, and
$p = 0$, 1, or 2.

The compounds are especially suitable for use in neutral or alkaline food compositions.

DETAILED DESCRIPTION OF THE INVENTION

The compounds of this invention, herein referred to as acid-hydrolyzable ester derivatives, comprise compounds having two alkyl groups bearing pendant ester groups, aliphatic groups, or acyl groups, or mixtures thereof, linked together by means of an acid labile linkage of the formula

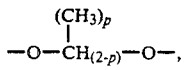

where $p = 0$ to 2.

The compounds of this invention may be defined by the formula

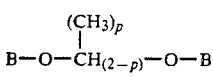

where

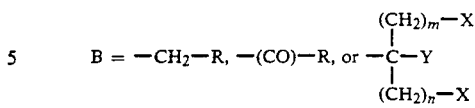

$X = H$, an alkyl having 1 to 4 carbons, —O—(CO)—R, or —(CO)—O—R, or mixtures thereof,
$Y = H$, an alkyl having 1 to 4 carbons, or —(CO)—O—R,
$R =$ an aliphatic group having 1 to 29 carbons,
$m = 0$, 1, or 2,
$n = 0$, 1, or 2, and
$p = 0$, 1, or 2.

The compounds are partially digestible and are especially suitable in neutral or alkaline foods.

The compounds of this invention have an acid-hydrolyzable linkage —O—(C(CH$_3$) —O—, where $p = 0$, 1, or 2, linking two alkyl groups bearing pendant ester groups, aliphatic groups, or acyl groups, or mixtures thereof. Thus, this invention encompasses compounds having acid-hydrolyzable linkages —O—CH$_2$—O— (when $p = 0$), —O—CH(CH$_3$)—O— (when $p = 1$) and —O—C(CH$_3$)$_2$—O— (when $p = 2$).

By "acid-hydrolyzable linkage" is meant a linkage that may be nonenzymatically decomposed in the presence of water at pH values commonly found in the stomach and upper gastrointestinal tract. Many of the acid-hydrolyzable linkages of this invention, for example, may, in an aqueous environment, spontaneously decompose at a pH of 2.0 to 3.0.

The acid-hydrolyzable linkage bridges two substituents (B in the formula above). The B substituents may be any one of three types: alkyl groups bearing pendant ester groups, aliphatic groups, or acyl groups, or mixtures thereof. The alkyl groups bearing pendant ester groups have the formula

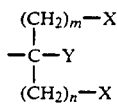

where m, X, and Y are as defined above.

This type of linked substituent comprises a central carbon bearing two X groups, each of which may have one or two (m or n) intervening methylene groups (—CH$_2$—). X may be a hydrogen in conventional ester linkage as compared to triglycerides (—O—(CO)—R) or an R group attached in reversed ester linkage as compared to triglycerides (—(CO)—O—R).

Aliphatic R groups so attached may be straight chain or branched, saturated or unsaturated. Aliphatic R groups attached in conventional ester linkage (—O—(CO)—R) are generally derived by acylating an hydroxyl (attached to the central carbon with or without one or two intervening methylene groups) with fatty acids. By the term "fatty acids" is meant synthetic or natural organic acids of the formula RCOOH. Examples of fatty acids include, but are not limited to, acetic, propionic, butyric, caproic, caprylic, pelargonic, capric, undecanoic, lauric, myristic, palmitic, stearic, arachidic, behenic, lignoceric, cerotic, montanic, melissic, palmitoleic, oleic, vaccenic, linoleic, linolenic, eleostearic, arachidonic, nervonic, eicosapentaenoic, docosatetraenoic, docosapentaenoic, docosahexaenoic, and the like acids.

Mixtures of fatty acids may also be used, such as those obtained from non-hydrogenated, partially hydrogenated or fully hydrogenated soybean, safflower, sunflower, high oleic sunflower, sesame, peanut, corn, olive, rice bran, canola, babassu nut, coconut, palm, palm kernel, lupin, nasturtium seed, mustard seed, cottonseed, low erucic rapeseed, meadow-foam, dairy butter or marine oils. Fatty acids derived from tallow or lard, or plant waxes such as jojoba may be employed. Specific fractions of natural or processed oils, fats or waxes may also be used. For example, high melting (~37° to 40° C. and above), medium melting (−20° to 40° C.) and low melting (below 20° C.) fractions may be desirable for certain applications.

When R is attached in reversed ester linkage (—(CO)—O—R), it may be derived by esterifying a carboxylic acid group (attached to the central carbon with or without one or two intervening methylene groups) with a fatty alcohol of the formula RCH2OH. Examples of fatty alcohols include the fatty alcohol counterparts of the fatty acids enumerated above, namely, ethyl, propyl, butyl, caproyl, caprylyl, pelargonyl, capryl, lauryl, undecanyl, myristyl, palmityl, stearyl, arachidyl, behenyl, lignoceryl, cerotyl, montanyl, melissyl, palmitoleyl, oleyl, vaccenyl, linoleyl, linolenyl, eleostearyl, arachidyl, nervonyl, eicosapaentanyl, docosatetraenoyl, docosapentaenyl, and docosahexaenoyl alcohols. Mixtures of fatty alcohols may also be used, such as those obtained from the processed or unprocessed natural oils enumerated above, or specific fractions of the oils.

The central carbon of this type of substituent also bears one Y group. Y may be a hydrogen (H), an alkyl having 1 to 4 carbons, or an R group attached in reversed ester linkage as compared to triglycerides (—(CO)—O—R).

Where B is an aliphatic group (—CH$_2$—R), it may be derived from a fatty alcohol of the formula RCH$_2$OH, defined above. Where B is an acyl group (—(CO)—R), it may be derived from a fatty acid of the formula RCOOH, defined above. Thus, the acid-hydrolyzable linkages of this invention may bridge fatty acids, fatty alcohols, or mixtures of these.

The R, X and Y groups will be selected to provide a discernible fatty character in the compounds. Thus, most of the R groups have 2 to 4 or more carbon atoms, with a majority containing 3 to 23, more narrowly 11 to 17, and even more narrowly, 13 to 17 carbon atoms (derived from fatty acids having 14 to 18 carbons). Preferred fat mimetics can have an array of R groups selected to include 95% or more having 13 to 17 carbon atoms. In one embodiment, the R groups may be predominantly saturated $C_{13}$ to $C_{17}$ groups. In another embodiment, the R groups may be predominantly unsaturated $C_{15}$ to $C_{17}$ groups (with a preponderance of monounsaturated groups).

R, X and Y groups derived from natural or processed oils, or fractions thereof, may be selected for specific functional properties desired in the food products incorporating the mimetics. For chocolate or confectionery applications, for example, R, X, and Y may be derived from high melting fractions; for chocolate applications, fractions that contract on solidification are especially desirable (rendering products easy to demold). For salad oil applications, R, X and Y may employ medium melting fractions that do not readily crystallize upon refrigeration. Margarine, cheese, frosting, and filling applications may employ groups derived from plastic fats or fractions, bakery products may employ groups stable to oxidation on storage, and so forth.

The choice, number and arrangement R, X, and Y groups will also be selected to affect the biological properties of the compounds. Since the acid-hydrolyzable linkage is generally cleaved in the digestive tract, the compounds are partially digestible, yielding B fragments. The B fragments may comprise more or less digestible substituents. The compounds of this invention preferably deliver less than 9 kcal/gram, more preferably below 6 kcal/gram, upon being metabolized.

An advantage of the present invention is that the caloric availability of the ester derivatives may be modulated by the linkage attaching the R groups as well as the selection of R groups. For example, caloric availability may be decreased by having at least one R group attached in reversed ester linkage to an alkyl. Alternatively, since long-chain saturated fatty acids are less well absorbed (Hashim, S. A., and Babayan, V. K., 31 Am. J. Clin. Nutr. S273-276 (1978)), a selection of these as R groups may be employed to decrease digestibility where the attachment is in conventional ester linkage (—O—(CO)—R) as compared to natural triglycerides.

Another advantage of the present invention is that, where an R group is metabolized, it may be a highly desirable or essential fatty acid such as linoleic acid.

The acid hydrolyzable ester derivatives of this invention may be incorporated either alone, or in combination with another fat and/or fat mimetic, into any food composition comprising fat ingredients and nonfat ingredients, or used in conjunction with any edible material. Other fats include natural triglycerides rich in highly desirable or essential fatty acids, such as oleic, linoleic, linolenic, or eicosapentaenoic acid, triglycerides bearing fatty acids having beneficial attributes such as those associated with conjugated linoleic acid isomers, medium chain triglycerides and the like. Other fat mimetics include any heretofore suggested as edible fat replacements, including, but not limited to, sugar esters, neoalkyl esters, polyglycerol esters, malonate esters, propoxylated glycerols, retrofats, carboxy/carboxylates, polyvinyl alcohol esters and the like.

The term "edible material" is broad and includes anything edible, whether or not intended for nutrition, e.g., it can be an additive such as an antioxidant for fats or oils, an antispatter agent, an emulsifier, a texture modifier such as a plasticizer for chewing gum, a component for cosmetics, or other minor functional ingredient such as a carrier or diluent for use in flavorings, pharmaceuticals, and the like.

Representative of fat-containing edible materials which can contain, in addition to other food ingredients, the fat mimetic compounds of this invention in full or partial replacement of natural or synthetic fat are: frozen desserts, e.g., sherbet, ice cream, ices, or milk shakes; puddings and pie fillings; margarine substitutes or blends; flavored bread or biscuit spreads; mayonnaises and mustards; filled dairy products such as filled cream or filled milk; dairy or nondairy cheese spreads; coffee lighteners, liquid and dried; flavored dips; frying fats and oils; reformed and comminuted meats; meat substitutes or extenders; egg products and substitutes; nut products such as peanut butter; pet foods; whipped toppings; compound coatings; frostings and fillings; cocoa butter replacements or blends; candy, especially fatty candies such as those containing peanut butter or chocolate; vegetable and fruit products; chewing gum;

breakfast cereals; bakery products, e.g., cakes, breads, rolls, pastries, cookies, biscuits, and savory crackers; mixes or ingredient premixes for any of these; as well as flavor, nutrient, drug or functional additive delivery systems. Preferred food compositions are neutral to alkaline.

The following is a list of representative, but not limiting, examples of acid hydrolyzable ester derivatives of this invention:

(A) Acid-hydrolyzable derivatives wherein the acid-hydrolyzable linkage bridges an acid B residue (R—(CO)—O—) and an alcohol B residue (denoted below as B'). This type of derivative may be described by the formula

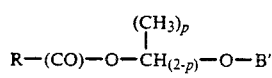

where

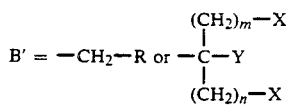

and X, Y, R, m, n, and p are as defined above.

Examples of this type of acid-hydrolyzable derivative include:

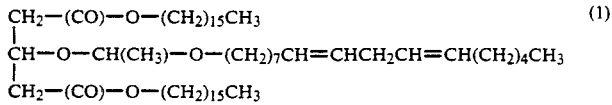
(1)

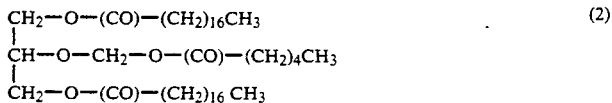
(2)

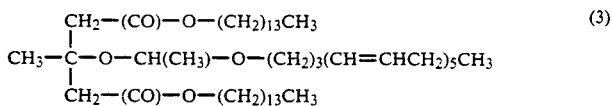
(3)

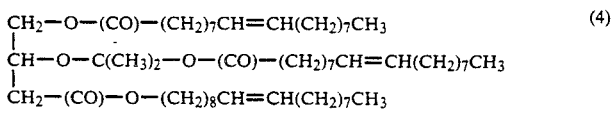
(4)

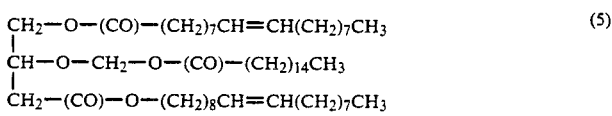
(5)

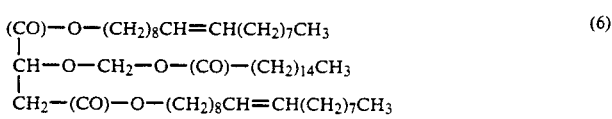
(6)

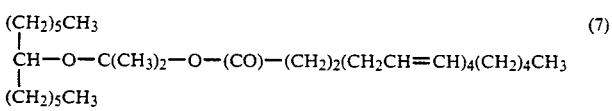
(7)

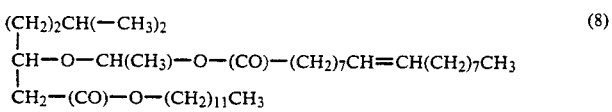
(8)

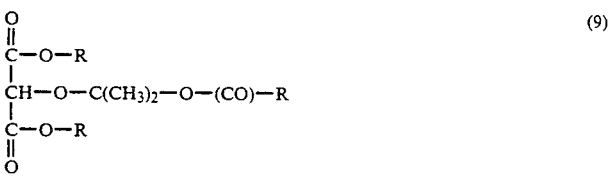
(9)

where the R groups are derived from soybean oil

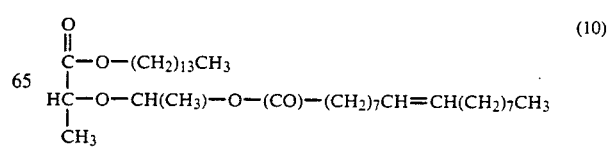
(10)

-continued

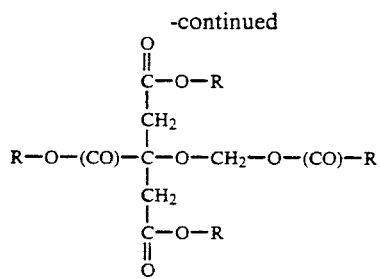
(11)

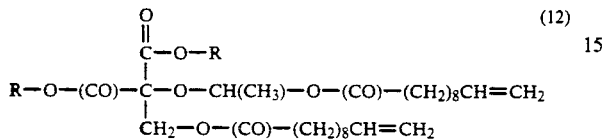
(12)

where the R groups are derived from partially hydrogenated corn oil

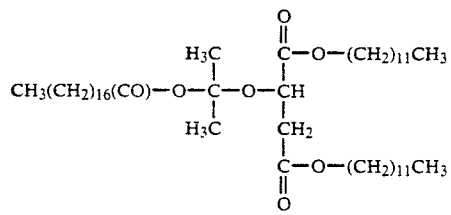
(13)

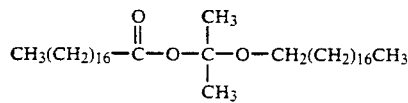
(14)

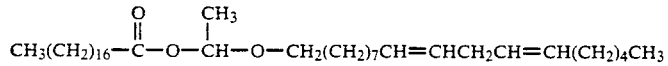
(15)

When B' is not —CH₂—R, the compounds may be synthesized by reacting a compound the formula

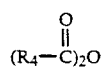

with a compound of the formula

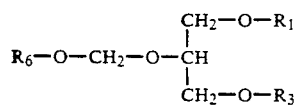

to yield a compound of the formula

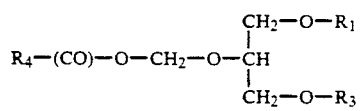

where $R_1$ and $R_3$ are hydrogen, alkyl, or acyl, and $R_4$ and $R_6$ are lower alkyls, in the presence of a catalytic amount of a Lewis acid as described, for example, in Eur. Pat. No. 187,297 to Morgans and Chapman (page 3, lines 15 to 32). Other syntheses are set out in the Examples that follow.

When B' is —CH₂—R, the compounds may be prepared in an analogous synthetic sequence by reacting a compound of the formula

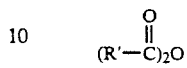

with a compound of the formula

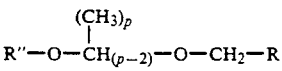

to yield a compound of the formula

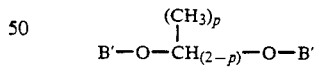

where R' is a lower alkyl, and R and p are as defined above.

(B) Acid-hydrolyzable derivatives wherein the acid-hydrolyzable linkage bridges two alcohol B residues (denotes below as B'). This type of derivative may be described by the formula $$B'-O-CH_{(2-p)}-O-B'$$
$$\overset{(CH_3)_p}{|}$$

where

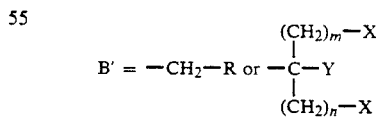

and X, Y, R, m, n, and p are as defined above.

Examples of this type of acid-hydrolyzable derivative include:

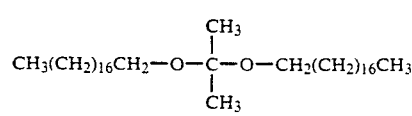
(16)

-continued

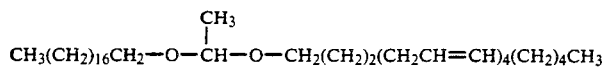  (17)

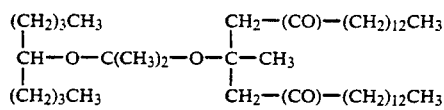  (18)

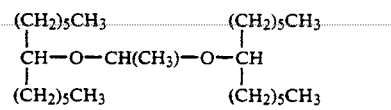  (19)

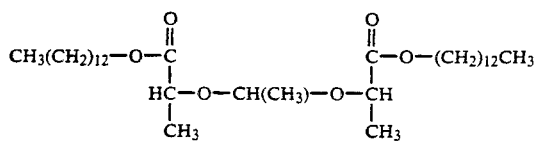  (20)

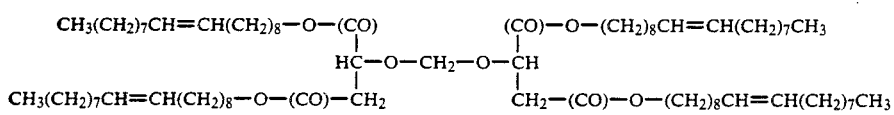  (21)

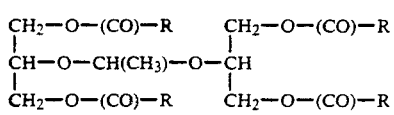  (22)

where the R groups are derived from partially hydrogenated canola oil

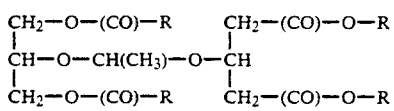  (23)

where the R groups are derived from high oleoic sunflower oil (C) Acid-hydrolyzable derivatives wherein the acid-hydrolyzable linkage bridges two acid B residues. This type of derivative may be described by the formula

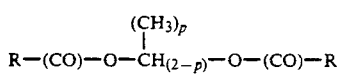

where and R, m, n, and p are as defined above.

Examples of this type of acid-hydrolyzable derivative include

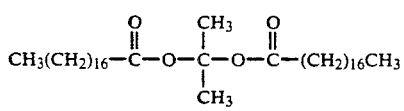  (24)

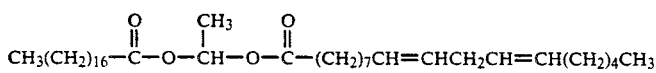  (25)

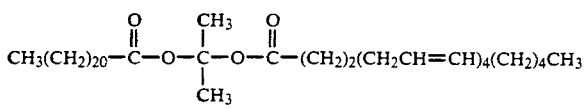  (26)

Any of the above compounds can be prepared with modified properties by substituting any of the specific R, X, or Y groups with any other disclosed above, including mixtures derived from natural sources. For example, the last compound can be prepared with a mixture derived from high oleic sunflower oil.

EXAMPLES

The following examples are presented to further illustrate and explain the present invention and should not be taken as limiting in any regard. Unless otherwise indicated, all parts and percentages are by weight, and are based on the weight at the particular stage of the processing being described.

EXAMPLE 1

In this example, 1,3-distearoyl-2-hexanoyloxymethyl-glycerol, an acid hydrolyzable fat mimetic depicted in structure (2) above, is prepared in four steps.

Step 1. Glycidol stearate. Glycidol stearate is prepared as described by Sasson, et al., *Ind. Eng. Chem. Prod. Res. Deve.*, 23:452 (1984).

Step 2. 1,3-Disteroylglycerol. A mixture of 171.3 g (0.5 mole) glycidol stearate, 156.5 g (0.55 mole) stearic acid, 1.0 g (0.025 mole) sodium hydroxide, and tetrabutylammonium hydrogensulfate (8.5 g, 0.025 mole)

in 400 mL ethanol is heated at reflux (80° C.) for 20 hours. The solid material is removed by passage of the reaction mixture through a short column of silica gel. After evaporation, the crude solid product is subjected to centrifugal partition chromatography using a mixture of acetonitrile-hexane. Recrystallization of the resulting powder from acetone-water gives 1,3-distearoylglycerol.

Step 3. 1,3-Distearoyl-2-chloromethylglycerol. Dry hydrogen chloride gas is bubbled through a solution of 1,3-distearoylglycerol (125 g, 0.2 mole) and 12 g (0.4 mole) paraformaldehyde in 700 mL dichloroethane for 1.5 hours at 0° C. Filtration and evaporation of solvent in vacuuo gives the title compound in quantitative yield.

Step 4. 1,3-Distearoyl-2-hexanoyloxymethylglycerol. To a solution of 101 g (0.15 mole) 1,3-distearoyl-2-chloromethylglycerol in 1000 mL dimethylformamide contained in a 2000-mL flask fitted with a reflux condenser protected with a $CaSO_4$ filled drying tube is added 27.6 g (0.2 mole) sodium hexanoate. After stirring at 25° C. for 17 hours, the solvent is removed in vacuuo and the oily residue is dissolved in diethyl ether. The ether solution is successively washed with water, 5% NaCl solution, and then is dried over anhydrous sodium sulfate. Filtration and concentration of the filtrate affords an oily solid which is steam deodorized to give a solvent free product yield.

EXAMPLE 2

This example describes a four-step synthesis of dioleyl 3-palmitoyloxymethyloxyglutarate, an acid-hydrolyzable fat mimetic depicted in structure (5) above.

Step 1. Dioleyl 1,3-acetonedicarboxylate. Trichloroacetic acid (9.8 g, 0.06 mole), dimethyl 1,3-acetonedicarboxylate (139.3 g, 0.80 mole), and oleyl alcohol (415.1 g, 1.68 mole, 5% excess) are combined in a 2000-mL flask fitted with a distillation head, thermometer, and teflon coated stirrer bar. The system is evacuated to ~150 Torr and is heated at 130°–40° C. for 17 hours. The yield of clear orange oil is quantitative.

Step 2. Dioleyl 3-hydroxyglutarate. Sodium borohydride (46.36 g, 1.22 mole) in 800 mL ice water and dioleyl 1,3-acetonedicarboxylate (525.0 g, ~0.81 mole) in 800 mL diethyl ether are combined in a 3000-mL flask fitted with a magnetic stirrer bar and a thermometer, and this mixture is stirred vigorously at ambient temperature for 22.5 hours. The ether layer is separated and washed twice with 800 mL portions of 5% hydrochloric acid, then twice with 800 mL portions of distilled water. The ether solution is dried over anhydrous $MgSO_4$, is filtered and evaporated to give 504.3 g of clear straw colored oil. Molecular distillation (168° C., ~0.8 Torr) affords pure diester alcohol product which is free of contaminating oleyl alcohol.

Step 3. Dioleyl 3-chloromethyloxglutarate. Dry hydrogen chloride gas is bubbled through a solution of dioleyl 3-hydroxyglutrate (389.4 g, 0.6 mole) and 36 g (1.2 mole) and 36 g (1.2 mole) paraformaldehyde in 2000 mL dichloroethane for 1.5 hours at 0° C. The reaction mixture is then stoppered and allowed to stand for 25 hours at 4° C., then is dried over anhydrous magnesium sulfate at 20° C. Filtration an evaporation of solvent in vacuuo gives the title compound in quantitative yield.

Step 4. Dioleyl 3-palmitoyloxymethyloxyglutarate. To a solution of 209 g (0.3 mole) dioleyl 3-chloromethyloxyglutarate in 2000 mL dimethylformamide contained in a 5000-mL flask fitted with a reflux condenser protected with a $CaSO_4$ filled drying tube is added 97.5 g (0.35 mole) sodium palmitate. After stirring at 25° C. for 17 hours, the solvent is removed in vacuuo and the oily residue is dissolved in diethyl ether. The ether solution is successively washed with water, 5% NaCl solution, and then is dried over anhydrous sodium sulfate. Filtration and concentration of the filtrate affords an oily solid which is steam deodorized to give a solvent free product.

EXAMPLE 3

Dioleyl 2-steroyloxymethyloxysuccinate, an acid hydrolyzable fat mimetic depicted in structure (6) above, is prepared in three steps.

Step 1. Dioleyl malate. D,L-malic acid (134.2 g, 1.00 mole) and oleyl alcohol (458.0 g. 1.70 mole) are combined in a 2000-mL flask fitted with a distillation head, thermometer, and teflon coated stirrer bar. The system is evacuated to ~150 Torr and is heated at 130°–140° C. for 17.5 hours. The orange oil obtained is passed through a falling film still to remove unreacted oleyl alcohol.

Step 2. Dioleyl 2-chloromethyloxysuccinate. Dry hydrogen chloride gas is bubbled through a solution of dioleyl malate (190.5 g, 0.3 mole) and 18 g (0.6 mole) paraformaldehyde in 1000 mL dichloroethane for 1.5 hours at 0° C. The reaction mixture is then stoppered and allowed to stand for 16 hours at 4° C, then is dried over anhydrous magnesium sulfate at 20° C. Filtration and evaporation of solvent in vacuuo gives the title compound in quantitative yield.

Step 3. Dioleyl 3-palmitoyloxymethyloxyglutarate. To a solution of 136.6 g (0.2 mole) dioleyl 2-chloromethyloxysuccinate in 1400 mL dimethylformamide contained in a 3000-mL flask fitted with a reflux condenser protected with a $CaSO_4$ filled drying tube is added 70.5 g (0.23 mole) sodium stearate. After stirring at 25° C. for 19 hours, the solvent is removed in vacuuo and the oily residue is dissolved in diethyl ether. The ether solution is successively washed with water, 5% NaCl solution, and then is dried over anhydrous sodium sulfate. Filtration and concentration of the filtrate affords an oily solid which is steam deodorized to give a solvent free product.

EXAMPLE 4

In this example, didodecyl 2-(2-steroyloxypropyl)oxysuccinate, an acid hydrolyzable fat mimetic depicted in structure (13) above, is prepared in three steps.

Step 1. Didoecyl malate. D,L-malic acid (302.2 g, 2.25 mole) and 931.9 g (5.00 mole) dodecanol are combined in a 3000-mL flask containing a magnetic stirrer bar and fitted with a thermometer and a vacuum distillation head. The apparatus is placed under about 170 Torr vacuum and warmed to 135° C. for 6.5 hours. Water distills from the reaction mixture under these conditions. The mixture is cooled to 60° C., and is passed twice through a falling film still (168° C., 0.8 Torr) to give the title composition as a white solid.

Step 2. Didodecyl 2-(2-chloropropyl)oxysuccinate. Dry hydrogen chloride gas is bubbled through a solution of didodecyl malate (117.7 g, 0.25 mole) and 15 g (0.5 mole) paraformaldehyde in 1000 mL dichloroethane for 1.5 hours at 0° C. The reaction mixture is then stoppered and allowed to stand for 16 hours at 4° C., then is dried over anhydrous magnesium sulfate at 20° C. Filtration and evaporation of solvent in vacuuo gives the title compound in quantitative yield.

Step 3. Didodecyl 2-(2-stearoyloxpropyl) oxysuccinate. To a solution of 129.7 g (0.25 mole) didodecyl 2-(2-chloropropyl)oxysuccinate in 1500 mL dimethylformamide contained in a 3000-mL flask fitted with a reflux condenser protected with a CaSO$_4$ filled drying tube is added 91.9 g (0.3 mole) sodium stearate. After stirring at 25° C. for 24 hours, the solvent is removed in vacuuo and the oily residue is dissolved in diethyl ether. The ether solution is successively washed with water, 5% NaCl solution, and then is dried over anhydrous sodium sulfate. Filtration and concentration of the filtrate affords an oily solid which is steam deodorized to give a solvent free product.

EXAMPLE 5

Frying Oil.

A frying oil may be prepared by adding 1 ppm polydimethylsiloxane to the fat mimetic of Example 3.

EXAMPLE 6

Potato Chips.

Whole peeled potatoes may be sliced, washed in water, and fried in the fat mimetic of Example 4 at 375° F. to desired color. The excess oil is shaken off and the chips are salted. The finished product contains about 35% fat mimetic.

EXAMPLE 7

Margarine.

A margarine may be prepared by emulsifying

| | parts |
|---|---|
| Oil Phase Ingredients | |
| Fat Mimetic of Example 1 | 34.3 |
| Fat Mimetic of Example 2 | 34.3 |
| Liquid Corn Oil | 0.55 |
| Partially Hydrogenated Corn Oil | 0.45 |
| Lecithin | 0.30 |
| Mono- and Di-Glycerides | 0.21 |
| Margarine Flavor and Color | 0.0062 |
| Aqueous Phase Ingredients | |
| Water | 25.8 |
| Whey | 1.00 |
| Salt | 2.00 |
| Sodium Benzoate | 0.086 |
| Potassium sorbate | 0.066 |
| CaEDTA | 0.0015 |

EXAMPLE 8

Ice Cream.

Vanilla ice cream may be prepared by mixing

| Ingredient | parts |
|---|---|
| Sugar (10X) | 15.0 |
| Nonfat Dry Milk | 3.9 |
| Salt | 0.4 |
| into Water | 39.0 | for 3 minutes. Then add melted

| Example 1 Fat Mimetic | 28.4 |
|---|---| and cook to 200° F. while mixing. Hold for 1 minute. Cool to 160° F., and add

| Sugared Egg Yolks | 12.5 |
|---|---|
| Vanilla Extract | 0.8 | and mix 1 minute. Cool and freeze to desired overrun.

EXAMPLE 9

Filled Cream.

To make a "filled cream" composition, homogenize about

| Ingredient | parts |
|---|---|
| Example 3 Fat Mimetic | 30.0 |
| Skim Milk | 69.9 |
| Polysorbate 80 | 0.1 | in a conventional dairy homogenizer.

EXAMPLE 8

Filled Milk.

To prepare a "filled milk" composition, combine about

| Ingredient | parts |
|---|---|
| Example 7 Filled Cream | 100 |
| Skim Milk | 900 | and rehomogenize.

EXAMPLE 9

Low Calorie Milk.

A low calorie "whole milk" may be prepared by combining

| Ingredient | parts |
|---|---|
| Nonfat Milk | 96.4 |
| Fat Mimetic of Example 3 | 3.5 |
| Lecithin | 0.1 | mixing and homogenizing.

EXAMPLE 10

Vanilla Wafers.

Vanilla wafers may be prepared by combining and mixing well

| Ingredient | parts |
|---|---|
| Flour | 40.0 |
| Sugar (10X) | 28.0 |
| Example 9 Fat Mimetic | 13.0 |
| Frozen Whole Eggs | 6.0 |
| High Fructose Corn Syrup | 4.0 |
| Salt | 0.7 |
| Vanilla | 0.3 |
| Sodium Bicarbonate | 0.3 |
| Sodium Aluminum Phosphate | 0.1 |
| Ammonium Bicarbonate | 0.1 |
| Water | 7.5 | aerating, and depositing onto a baking surface and baking in the usual manner.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims.

What is claimed is:

1. A food composition comprising fat ingredients and nonfat ingredients, wherein said fat ingredients are partially or fully replaced by a fat mimetic compound of the formula

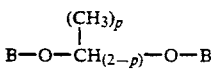

where

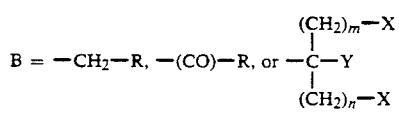

X = H, an alkyl having 1 to 4 carbons, —O—(CO)—R, or —(CO)—O—R, or mixtures thereof,
Y = H, an alkyl having 1 to 4 carbons, or —(CO)—O—R,
R = an aliphatic group having 1 to 29 carbons,
m = 0, 1, or 2,
n = 0, 1, or 2, and
p = 0, 1 or 2.

2. A composition according to claim 1 wherein the R groups have 3 to 23 carbon atoms.

3. A composition according to claim 1 wherein the R groups are derived from fatty acids selected from the group consisting of acetic, propionic, butyric, caproic, caprylic, pelargonic, capric, undecanoic, lauric, myristic, palmitic, stearic, arachidic, behenic, lignoceric, cerotic, montanic, melissic, palmitoleic, oleic, vaccenic, linoleic, linolenic, eleostearic, arachidonic, erucic, brassidic, nervonic, eicosapentaenoic, docosatetraenoic, docosapentaenoic, and docosahexaenoic acids, their alcohol counterparts, and mixtures thereof.

4. A composition according to claim 1 wherein the R groups are derived from mixtures obtained from the hydrolysis of unhydrogenated, partially hydrogenated, or fully hydrogenated oils selected from the group consisting of soybean, safflower, sunflower, high oleic sunflower, sesame, peanut, corn, olive, rice bran, canola, babassu nut, coconut, palm, palm kernel, lupin, nasturtium seed, mustard seed, cottonseed, low erucic rapeseed, meadowfoam, dairy butter and marine oils, and fractions thereof.

5. A composition according to claim 1 wherein said fat mimetic has the formula

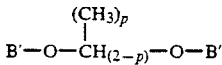

where

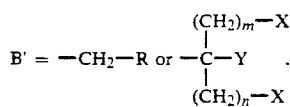

6. A composition according to claim 1 wherein said fat mimetic has the formula

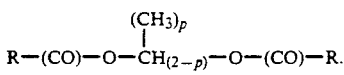

7. A composition according to claim 1 wherein said fat mimetic has the formula

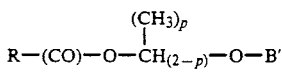

where

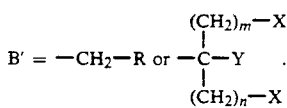

8. A composition according to claim 7 wherein

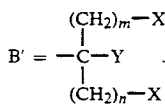

9. A composition according to claim 8 wherein at least one X is —(CO)—O—R.

10. A composition according to claim 8 wherein Y is H.

11. A composition according to claim 8 wherein m=1, n=1, both X groups are -O—(CO)—R and Y is H.

12. A composition according to claim 10 wherein p=1 or 2.

13. A method for preparing an edible composition having a digestible fat component comprising incorporating into said composition a compound of the formula

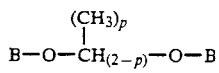

where

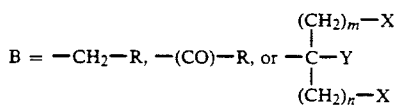

X = H, an alkyl having 1 to 4 carbons, —O—(CO)—R, or —(CO)—O—R, or mixtures thereof,
Y = H, an alkyl having 1 to 4 carbons, or —(CO)—O—R,
R = an aliphatic group having 1 to 29 carbons,
m = 0, 1, or 2,
n = 0, 1, or 2, and
p = 0, 1, or 2, in full or partial replacement of said digestible fat component.

14. A method for reducing the available calories in a food composition having an edible fat component, which method comprises replacing at least a portion of said edible fat component with a compound of the formula $$B-O-\underset{\underset{(CH_3)_p}{|}}{CH_{(2-p)}}-O-B$$

where $$B = -CH_2-R,\ -(CO)-R,\ or\ -\underset{\underset{(CH_2)_n-X}{|}}{\overset{\overset{(CH_2)_m-X}{|}}{C}}-Y$$

X=H, an alkyl having 1 to 4 carbons, —O—(-CO)—R, or —(CO)—O—R, or mixtures thereof,
Y=H, an alkyl having 1 to 4 carbons, or —(-CO)—O—R,
R=an aliphatic group having 1 to 29 carbons,
m=0, 1, or 2,
n=0, 1, or 2, and
p=0, 1, or 2.

15. A method according to claim 14 wherein said compound delivers less than 6 kcal/gram upon being metabolized.

16. A method according to claims 13 or 14 wherein the R groups are derived from fatty acids selected from the group consisting of acetic, propionic, butyric, caproic, caprylic, pelargonic, capric, undecanoic, lauric, myristic, palmitic, stearic, arachidic, behenic, lignoceric, cerotic, montanic, melissic, palmitoleic, oleic, vaccenic, linoleic, linolenic, eleostearic, arachidonic, erucic, brassidic, nervonic, eicosapentaenoic, docosatetraenoic, docosapentaenoic, and docosahexaenoic acids, and mixtures thereof.

17. A method according to claims 13 or 14 wherein the R groups are derived from ixtures obtained from the hydrolysis of unhydrogenated, partially hydrogenated, or fully hydrogenated oils selected from the group consisting of soybean, safflower, sunflower, high oleic sunflower, sesame, peanut, corn, olive, rice bran, canola, babassu nut, coconut, palm, palm kernel, lupin, nasturtium seed, mustard seed, cottonseed, low erucic rapeseed, meadowfoam, dairy butter and marine oils, and fractions thereof.

18. A method according to claims 13 or 14 wherein wherein said compound has the formula $$R-(CO)-O-\underset{\underset{(CH_3)_p}{|}}{CH_{(2-p)}}-O-B'$$

where $$B' = -\underset{\underset{(CH_2)_n-X}{|}}{\overset{\overset{(CH_2)_m-X}{|}}{C}}-Y\ ,$$

at least one X is —(CO)—O—R, Y is H, and R has 3 to 23 carbons.

19. A method according to claims 13 or 14 wherein wherein said compound has the formula $$R-(CO)-O-\underset{\underset{(CH_3)_p}{|}}{CH_{(2-p)}}-O-B'$$

where $$B' = -\underset{\underset{(CH_2)_n-X}{|}}{\overset{\overset{(CH_2)_m-X}{|}}{C}}-Y\ ,$$

X=—O—(CO)—R, Y is H, R has 3 to 23 carbons, and m =n =1.

20. In a fat-containing food composition, an improvement wherein at least a portion of the fat is replaced by a compound of the formula $$R-(CO)-O-(C(CH_3)_pH_{2-p})-O-\underset{\underset{(CH_2)_n-X}{|}}{\overset{\overset{(CH_2)_m-X}{|}}{C}}-Y$$

where
X=H, an alkyl having 1 to 4 carbons, —O—(-CO)—R, or —(CO)—O—R, or mixtures thereof,
Y=H, an alkyl having 1 to 4 carbons, or —(-CO)—O—R,
R=an aliphatic group having 1 to 29 carbons,
m=0, 1, or 2,
n =0, 1, or 2, and
p =0, 1, or 2.

21. An improvement according to claim 20 wherein at least one X is —(CO)—O—R, Y is H, and R has 3 to 23 carbons.

22. An improvement according to claim 20 wherein both X groups are —O—(CO)—R, Y is H, and R has 3 to 23 carbons.

* * * * *